United States Patent
Zhang et al.

(10) Patent No.: US 12,204,862 B2
(45) Date of Patent: Jan. 21, 2025

(54) MODULAR SELF-SUPERVISION FOR DOCUMENT-LEVEL RELATION EXTRACTION

(71) Applicant: MICROSOFT TECHNOLOGY LICENSING, LLC, Redmond, WA (US)

(72) Inventors: Sheng Zhang, Issaquah, WA (US); Cliff Richard Wong, Seattle, WA (US); Naoto Usuyama, Bellevue, WA (US); Sarthak Jain, Boston, MA (US); Tristan Josef Naumann, Seattle, WA (US); Hoifung Poon, Bellevue, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 514 days.

(21) Appl. No.: 17/378,551

(22) Filed: Jul. 16, 2021

(65) Prior Publication Data
US 2023/0019081 A1    Jan. 19, 2023

(51) Int. Cl.
*G06F 40/30*    (2020.01)
*G06F 40/205*   (2020.01)
*G06N 20/00*    (2019.01)
*G16H 70/40*    (2018.01)

(52) U.S. Cl.
CPC ............ *G06F 40/30* (2020.01); *G06F 40/205* (2020.01); *G06N 20/00* (2019.01); *G16H 70/40* (2018.01)

(58) Field of Classification Search
CPC .............................. G06N 20/00; G16H 70/40
See application file for complete search history.

(56) References Cited

U.S. PATENT DOCUMENTS

| | | | | |
|---|---|---|---|---|
| 9,235,812 | B2 * | 1/2016 | Scholtes | G06N 20/00 |
| 2005/0102614 | A1 * | 5/2005 | Brockett | G06F 40/44 |
| | | | | 715/256 |
| 2018/0082183 | A1 | 3/2018 | Hertz et al. | |
| 2020/0311198 | A1 | 10/2020 | Poon et al. | |

(Continued)

OTHER PUBLICATIONS

Limin Yao, Aria Haghighi, Sebastian Riedel, and Andrew McCallum. 2011. Structured Relation Discovery using Generative Models. In Proceedings of the 2011 Conference on Empirical Methods in Natural Language Processing, pp. 1456-1466, Edinburgh, Scotland, UK. . . Association for Computational Linguistics. (Year: 2011).*

(Continued)

*Primary Examiner* — Jesse S Pullias
(74) *Attorney, Agent, or Firm* — Workman Nydegger

(57) ABSTRACT

Systems and methods are provided for generating and training a relation extraction model configured to extract document-level relations. Systems obtain a knowledge database that comprises a plurality of entity tuples and a plurality of relation types, use the knowledge database to generate annotated relation instances based on relation instances that are identified in a set of unlabeled text, generate a training dataset comprising the annotated relation instances and the set of unlabeled text, and generate the machine learning model via modular self-supervision. Systems and methods are also provided for using a relation extraction model to extract document-level relations in specific use scenarios, such as for extracting drug response relations from full-text medical research articles.

12 Claims, 11 Drawing Sheets

(56) References Cited

U.S. PATENT DOCUMENTS

| | | | |
|---|---|---|---|
| 2020/0334416 A1 | 10/2020 | Vianu et al. | |
| 2021/0142008 A1* | 5/2021 | Patra | G06F 40/237 |
| 2021/0241050 A1* | 8/2021 | Gunaratna | G06N 3/042 |
| 2022/0138599 A1* | 5/2022 | Aravamudan | G16B 50/00 706/55 |

OTHER PUBLICATIONS

Ng et al. "Improving Machine Learning Approaches to Coreference Resolution". Proceedings of the 40th Annual Meeting of the Association for Computational Linguistics (ACL), Philadelphia, Jul. 2002 (Year: 2002).*

"International Search Report and Written Opinion Issued in PCT Application No. PCT/US22/035887", Mailed Date: Oct. 19, 2022, 8 Pages.

Andreas, et al., "Neural Module Networks", In Proceedings of the IEEE Conference on Computer Vision and Pattern Recognition, Jun. 27, 2016, pp. 39-48.

Chakravarty, et al., "OncoKB: a Precision Oncology Knowledge Base", In Journal of JCO Precision Oncology, vol. 1, May 16, 2017, pp. 1-16.

Christopoulou, et al., "Connecting the Dots: Document-Level Neural Relation Extraction with Edge-Oriented Graphs", In Proceedings of the Conference on Empirical Methods in Natural Language Processing and the 9th International Joint Conference on Natural Language Processing, Nov. 3, 2019, pp. 4925-4936.

Craven, et al., "Constructing Biological Knowledge Bases by Extracting Information from Text Sources", In Proceedings of the Seventh International Conference on Intelligent Systems for Molecular Biology, Oct. 1, 1999, pp. 77-86.

Dienstmann, et al., "Database of Genomic Biomarkers for Cancer Drugs and Clinical Targetability in Solid Tumors", In Journal of Cancer Discovery, vol. 5, Issue 2, Feb. 1, 2015, pp. 118-124.

Gerber, et al., "Beyond NomBank: A Study of Implicit Arguments for Nominal Predicates", In Proceedings of the 48th Annual Meeting of the Association for Computational Linguistics, Jul. 11, 2010, pp. 1583-1592.

Gu, et al., "Domain-Specific Language Model Pretraining for Biomedical Natural Language Processing", In Repository of arXiv:2007.15779v1, Jul. 31, 2020, 22 Pages.

Jia, et al., "Document-Level N-ary Relation Extraction with Multiscale Representation Learning", In Proceedings of the Conference of the North American Chapter of the Association for Computational Linguistics: Human Language Technologies, vol. 1, Jun. 2, 2019, pp. 3693-3704.

Joshi, et al., "SpanBERT: Improving Pre-training by Representing and Predicting Spans", In Journal of Transactions of the Association for Computational Linguistics, vol. 8, Jan. 1, 2020, pp. 64-77.

Kipf, et al., "Semi-Supervised Classification with Graph Convolutional Networks", In Proceedings of the International Conference on Learning Representations, Feb. 22, 2017, 14 Pages.

Koch, et al., "Type-Aware Distantly Supervised Relation Extraction with Linked Arguments", In Proceedings of the Conference on Empirical Methods in Natural Language Processing, Oct. 25, 2014, pp. 1891-1901.

Lee, et al., "Higher-Order Coreference Resolution with Coarse-to-Fine Inference", In Proceedings of the Conference of the North American Chapter of the Association for Computational Linguistics: Human Language Technologies, vol. 2, Jun. 1, 2018, pp. 687-692.

Lee, et al., "Stanford's Multi-Pass Sieve Coreference Resolution System at the CoNLL-2011 Shared Task", In Proceedings of the Fifteenth Conference on Computational Natural Language Learning: Shared Task, Jun. 23, 2011, pp. 28-34.

Li, et al., "BioCreative V CDR Task Corpus: A Resource for Chemical Disease Relation Extraction", In Journal of Biological Databases and Curation, Apr. 11, 2016, pp. 1-10.

Loshchilov, et al., "Decoupled Weight Decay Regularization", In Repository of arXiv:1711.05101v3, Jan. 4, 2019, 19 Pages.

Mintz, et al., "Distant Supervision for Relation Extraction without Labeled Data", In Proceedings of the Joint Conference of the 47th Annual Meeting of the ACL and the 4th International Joint Conference on Natural Language Processing of the AFNLP, Aug. 2, 2009, pp. 1003-1011.

Parsons, Terence, "Events in the Semantics of English: A Study in Subatomic Semantics", In Publication of MIT Press, 1990, pp. 121-126.

Paszke, et al., "PyTorch: An Imperative Style, High-Performance Deep Learning Library", In Proceedings of the 33rd Conference on Neural Information Processing Systems, Dec. 8, 2019, 12 Pages.

Patterson, et al., "The Clinical Trial Landscape in Oncology and Connectivity of Somatic Mutational Profiles to Targeted Therapies", In Journal of Human Genomics, vol. 10, Issue 1, Jan. 16, 2016, 13 Pages.

Peng, et al., "Cross-Sentence N-ary Relation Extraction with Graph LSTMs", In Journal of Transactions of the Association for Computational Linguistics, vol. 5, Apr. 2017, pp. 101-116.

Pradhan, et al., "CoNLL-2012 Shared Task: Modeling Multilingual Unrestricted Coreference in OntoNotes", In Proceedings of Joint Conference on EMNLP and CoNLL-Shared Task, Association for Computational Linguistics, Jul. 13, 2012, 40 Pages.

Quirk, et al., "Distant Supervision for Relation Extraction beyond the Sentence Boundary", In Proceedings of the 15th Conference of the European Chapter of the Association for Computational Linguistics: vol. 1, Apr. 3, 2017, pp. 1171-1182.

Raghunathan, et al., "A Multi-Pass Sieve for Coreference Resolution", In Proceedings of the Conference on Empirical Methods in Natural Language Processing, Oct. 9. 2010, pp. 492-501.

Ratner, et al., "Snorkel: Rapid Training Data Creation with Weak Supervision", In Proceedings of the VLDB Endowment, vol. 11, Issue 3, Nov. 3, 2017, pp. 269-282.

Rocktäschel, et al., "End-to-End Differentiable Proving", In Proceedings of the 31st International Conference on Neural Information Processing Systems, Dec. 4, 2017, 13 Pages.

Surdeanu, et al., "Overview of the English Slot Filling Track at the TAC2014 Knowledge Base Population Evaluation", In Proceedings of the Text Analysis Conference, Mar. 14, 2014, 15 Pages.

Swampillai, et al., "Extracting Relations Within and Across Sentences", In Proceedings of the International Conference Recent Advances in Natural Language Processing, Sep. 12, 2011, pp. 25-32.

Vaswani, et al., "Attention Is All You Need", In Proceedings of the 31st Conference on Neural Information Processing Systems, Dec. 4, 2017, 11 Pages.

Verga, et al., "Simultaneously Self-Attending to All Mentions for Full-Abstract Biological Relation Extraction", In Proceedings of the Conference of the North American Chapter of the Association for Computational Linguistics: Human Language Technologies, vol. 1, Jun. 1, 2018, pp. 872-884.

Wang, et al., "Deep Probabilistic Logic: A Unifying Framework for Indirect Supervision", In Proceedings of the Conference on Empirical Methods in Natural Language Processing, Oct. 31, 2018, pp. 1891-1902.

Wick, et al., "Learning Field Compatibilities to Extract Database Records from Unstructured Text", In Proceedings of the Conference on Empirical Methods in Natural Language Processing, Jul. 22, 2006, pp. 603-611.

"The Clinical Knowledgebase (CKB)", Retrieved From: https://ckbhome.jax.org/, Retrieved Date: Jun. 21, 2021, 2 Pages.

Yang, et al., "Joint Extraction of Events and Entities within a Document Context", In Proceedings of the Conference of the North American Chapter of the Association for Computational Linguistics: Human Language Technologies, Jun. 12, 2016, pp. 289-299.

Yao, et al., "DocRED: A Large-Scale Document-Level Relation Extraction Dataset", In Proceedings of the 57th Annual Meeting of the Association for Computational Linguistics, Jul. 28, 2019, pp. 764-777.

Yoshikawa, et al., "Coreference Based Event-Argument Relation Extraction on Biomedical Text", In Journal of Biomedical Semantics, vol. 2, Issue 5, Oct. 6, 2011, 14 Pages.

(56) References Cited

OTHER PUBLICATIONS

Zeng, et al., "Double Graph Based Reasoning for Document-level Relation Extraction", In Proceedings of the Conference on Empirical Methods in Natural Language Processing, Nov. 16, 2020, pp. 1630-1640.

"CIVIC—Clinical Interpretation of Variants in Cancer", Retrieved From : https://civicdb.org/home, Retrieved Date: Jun. 21, 2021, 5 Pages.

"Project Hanover", Retrieved From: https://www.microsoft.com/en-us/research/project/project-hanover/, Jul. 4, 2016, 5 Pages.

Wu, et al., "Renet: A Deep Learning Approach for Extracting Gene-Disease Associations from Literature", In Proceedings of the International Conference on Research in Computational Molecular Biology, Apr. 2, 2019, pp. 272-284.

\* cited by examiner

"... The patient's peripheral blood indices are shown over time relative to the first dose of the MEK inhibitor cobimetinib ..."

(... 17 sentences spanning 2 paragraphs ...)

"... MAP2K1 mutations appeared later with p.K57T expanding to become the dominant clone ..."

(... 10 sentences spanning 3 paragraphs ...)

"... Expression of the MAP2K1 mutants in a lymphoid cell line showed that while each mutation was able to activate ERK in the presence of vemurafenib, all mutations remained sensitive to MEK inhibitors ..."

FIG. 5

MODULAR SELF-SUPERVISION FOR DOCUMENT-LEVEL RELATION EXTRACTION

BACKGROUND

Natural language understanding refers to a set of machine learning tasks for training machine learning models to understand text and spoken words in a manner similar to the way humans are able to understand text and spoken words. Relation extraction is a particular type of natural language understanding that includes the detection and classification of semantic relationships within portions of text. Relation extraction is a more complex task than entity linking because the computing system performing the relation extraction must identify the desired entities (e.g., entity linking), as well as to learn the relationships between the different entities. The term entity, in this regard, refers to a particular person, place, thing, action, or a particular word or phrase that represents an idea.

Conventional relation extraction systems are configured to extract relations between entities co-occurring within the same sentence, or within a set of consecutive sentences. In some instances, existing systems are also configured to identify and extract relations between entities co-occurring within a single paragraph.

Conventional approaches for performing relation extraction experience major challenges in both inference and learning. Despite some recent progress, there are still significant challenges, for example, with modeling long text spans using conventional neural architectures, such as the Long-Short Term Memory (LSTM) networks and Transformer models. Additionally, the data needed for direct supervision training of the models is scarce, and task-specific self-supervision, such as distant supervision, becomes extremely noisy when applied beyond short text spans.

Because of these significant challenges in modeling long text spans and obtaining high-quality supervision signals, document-level relation extraction has been relatively unexplored. Prior work often focuses on simple extensions of sentence-level extraction (e.g., by incorporating coreference annotations or considering special cases when document-level relations reduce to sentence-level attribution classification. Recently, cross-sentence relation extraction has seen increasing interest, but most efforts are still limited to short text spans contained within a single paragraph of text, such as consecutive sentences or abstracts.

While some work has considered processing of full-text articles containing hundreds of sentences, it has been found that in such work, the processing systems only model local text units in isolation and cannot effectively handle relations whose arguments never co-occur at the paragraph level (within a single/same paragraph).

The foregoing traditional relation extraction models, particularly when applied to large text spans, experience a significant waste of computational expense during text processing for at least the reasons mentioned above. Accordingly, there is an on-going need and desire for improved systems, methods, and devices for relation extraction, and particularly, for improved systems, methods, and devices that can be utilized to improve relation extraction at a document-level, so as to perform relation extraction more efficiently and effectively on large text spans in which entity relationships span different paragraphs.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

Embodiments disclosed herein relate to systems, methods, and devices that are configured to facilitate document-level relation extraction.

Disclosed systems are configured to obtain a knowledge database that comprises a plurality of entity tuples and a plurality of relation types. Each relation type included in the plurality of relation types corresponds to one or more entity tuples included in the plurality of entity tuples. The systems use the knowledge database to generate annotated relation instances based on relation instances that are identified in a set of unlabeled text and generate a training dataset comprising the annotated relation instances and the set of unlabeled text.

Disclosed systems also generate a machine learning relation extraction model by at least: (i) training a first machine learning module on the training dataset as a relation classifier configured to identify and classify one or more relation instances occurring at a text-span level within a document, wherein a text span is a predefined portion of text that is less than an entirety of the document, and (ii) training a second module as a resolution classifier configured to identify and classify a set of entity pairs occurring at a document-level from a plurality of entities identified throughout the entirety of the document, wherein the machine learning model is configured as a relation extraction model trained to perform modular document-level relation extraction for target relations associated with the document, including target relations that span different paragraphs within the document.

Some systems use the relation extraction model to extract relations at a document-level by at least first obtaining the relation extraction model comprising the aforementioned (i) relation classifier and (ii) resolution classifier. Then, the systems use the relation classifier to identify the target relation comprising one or more target entities and obtain a target document comprising unannotated text that is parsed into a plurality of text spans. Additionally, the systems also use the resolution classifier to identify a first set of entities corresponding to the target relation based on individually applying each text span included the plurality of text spans to the relation classifier. Each of these entities included in the first set of entities corresponds to a different entity included in the one or more target entities, and the first set of entities co-occurs within a particular text span included in the plurality of text spans. The systems also identify a second set of entities co-occurring within the document based on applying the target document to the resolution classifier in order to classify one or more pairs of related entities identified in the second set of entities according to one or more relation types of a plurality of relation types. Finally, the systems resolve one or more entities included in the first set of entities with one or more entities included in the second set of entities based on the one or more pairs of related entities and generate a final set of entities corresponding to the target relation based on the first set of entities and the one or more entities resolved from the second set of entities. The final set of resolved entities and their relationships may span different paragraphs within the document.

Disclosed embodiments include, but are not limited to, specific use scenarios such as methods for extracting a drug response relation from a document, wherein the drug response relation occurs at a document-level and that spans multiple different paragraphs in a document.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be obvious from the description, or may be learned by the practice of the teachings herein. Features and advantages of the invention may be realized and obtained by means of the instruments and combinations particularly pointed out in the appended claims. Features of the present invention will become more fully apparent from the following description and appended claims or may be learned by the practice of the invention as set forth hereinafter.

BRIEF DESCRIPTION OF THE DRAWINGS

In order to describe the manner in which the above-recited and other advantages and features can be obtained, a more particular description of the subject matter briefly described above will be rendered by reference to specific embodiments which are illustrated in the appended drawings. Understanding that these drawings depict only typical embodiments and are not therefore to be considered to be limiting in scope, embodiments will be described and explained with additional specificity and detail through the use of the accompanying drawings in which:

FIG. 5 illustrates an example embodiment for a document that comprises a drug-gene-mutation relation generated from entities that never co-occur within the same paragraph.

DETAILED DESCRIPTION

Figure 1:
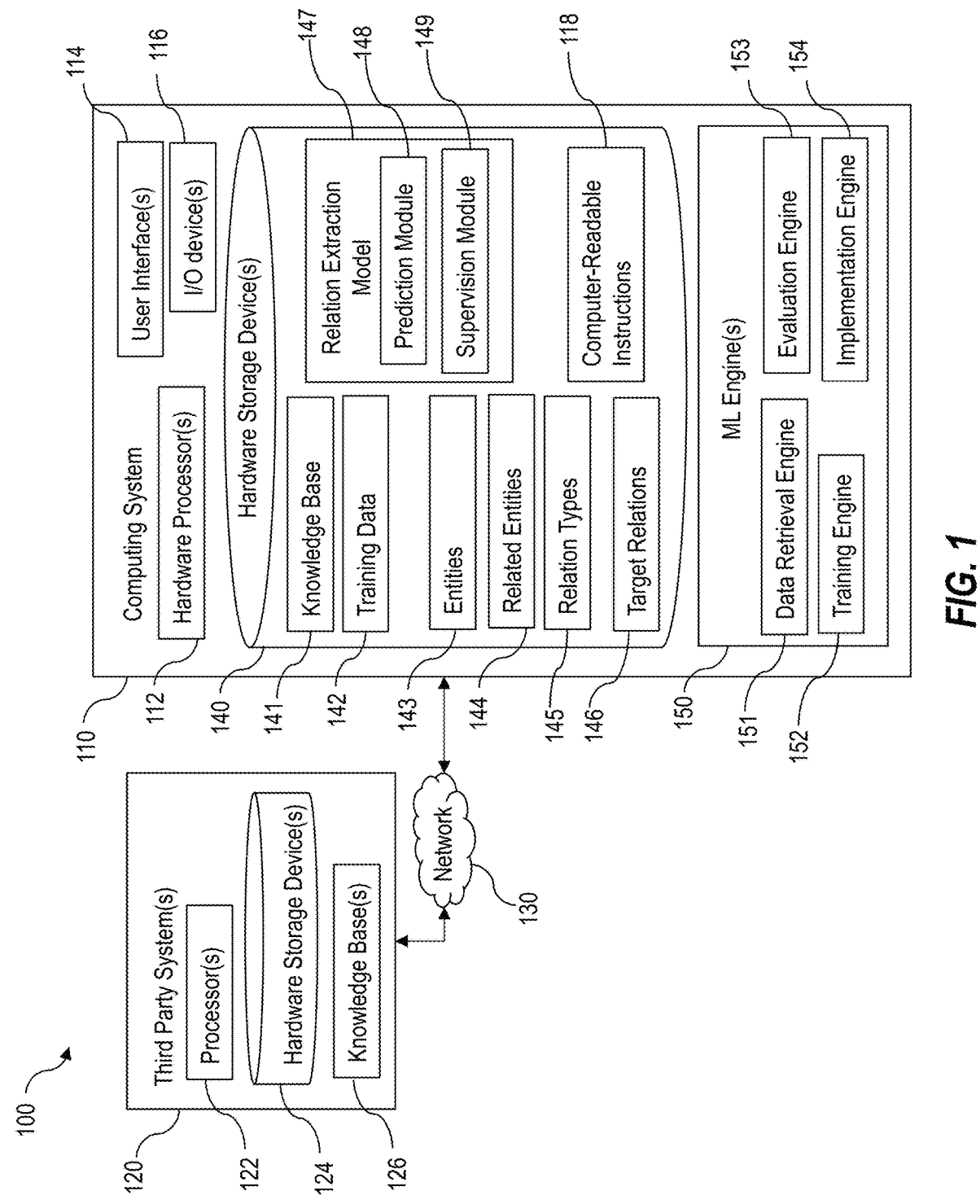
FIG. 1 illustrates an example architecture that includes a computing system that includes and/or that is capable of being utilized to implement the disclosed embodiments.

Embodiments disclosed herein relate to systems, methods, and devices that are configured to facilitate relation extraction during natural language processing, and even more particularly, for systems, methods, and devices that can be utilized to extract document-level relations. Disclosed embodiments are operable to facilitate document-level relation extraction by generating and training a modular machine learning model configured to extract document-level relations and trained using modular self-supervision.

The disclosed embodiments provide many technical advantages over existing systems, methods, and devices. For example, while prior work considers document-level extraction as a single monolithic problem in which systems are not able to efficiently identify and classify entity relationships spanning multiple different paragraphs, disclosed embodiments herein describe systems and methods for decomposing document-level relation extraction into relation extraction and argument resolution that enables more efficient and effective entity relation extraction and classification for related entities spanning different paragraphs in a document. By performing document-level relation extraction in this modular manner, the systems are able to incorporate discourse modeling and leverage modular self-supervision for each sub-problem, which is less noise-prone and can be further refined in end-to-end systems via variational EM. This configuration is especially beneficial for extraction relations that occur at a paragraph level (i.e., cross paragraph relation mentions).

By representing n-ary relations using Davidsonian semantics, relations including more than binary relationships are able to be modeled (e.g., ternary and higher order tuples). Furthermore, by combining paragraph-level relation classification with discourse or document-level argument resolution using global reasoning rules, each component problem resides in short text spans and their corresponding self-supervision is much less noisy and less error prone. Such approaches beneficially utilize modular neural networks and neural logic programming in order to decompose the complex task of document-level relation extraction into local neural learning and global structured integration.

Instead of training models from end-to-end direct supervision (which requires vast amounts of input-output data pairs as ground truth for the direct supervision training), modular self-supervision is applied for the different component problems, which is a more readily available method of training (e.g., is much less training data intensive as compared to direct supervision training). By applying deep probabilistic logic to combine the modular self-supervision techniques and joint inference with global reasoning rules, the trained models are able to handle long text spans, such as full-text articles, and also expand extraction to the significant portion of cross-paragraph relations that are out of reach to prior methods.

A popular type of evaluation metric for relation extraction models is a macro-averaged F1, which is averaged across various relationships. Where a thorough evaluation of models trained and implemented by the disclosed systems and methods herein was conducted, trained models outperformed conventional models, such as multi-scale learning and graph neural networks, by over 20 absolute F1 points. The gain is particularly pronounced among the most challenging relation instances whose arguments never co-occur in a paragraph.

Attention will now be first directed to FIG. 1, which illustrates a computing system 110 that may include or be used to implement aspects of the claimed invention. In particular, the computing system 110 is configured, as described throughout this disclosure, to generate, train, and operate a relation extraction model that is capable of extracting relations at a document-level that span different paragraphs of a subject document.

The computing system 110 is currently illustrated as part of a computing environment 100 that also includes third-party system(s) 120 (which can also be configured as remote systems) in communication (via a network 130) with computing system 110. These remote systems may include distributed portions of the computing system 110. Alternatively, or additionally, the third-party system(s) 120 include the third-party knowledge base(s) 126 that are referenced herein.

The computing system 110 is also illustrated as including one or more processor(s) (such as one or more hardware processor(s)) 112 and a storage (i.e., hardware storage device(s) 140) storing computer-readable instructions 118 wherein one or more of the hardware storage device(s) 140 is able to house any number of data types and any number of computer-readable instructions 118 by which the computing system 110 is configured to implement one or more aspects of the disclosed embodiments when the computer-readable instructions 118 are executed by the one or more processor(s) 112. The computing system 110 is also shown including user interface(s) 114 and input/output (I/O) device(s) 116.

Hardware storage device(s) 140 is currently shown as a single storage unit. However, it will be appreciated that the hardware storage device(s) 140 is/are also sometimes implemented as a distributed storage which is distributed throughout several separate and sometimes remote systems and/or third-party system(s) 120. In this regard, it will be appreciated that the computing system 110 can comprise a distributed system with one or more of the components of computing system 110 being maintained/run by different discrete systems that are remote from each other and that each perform different tasks. In some instances, for example, the computing system 110 operates as a plurality of distributed systems that perform similar and/or shared tasks for implementing the disclosed functionality, such as in a distributed cloud environment.

The hardware storage device(s) 140 are configured to store the different data types including knowledge base data 141, training data 142, entities 143, related entities 144, relation types 145, and target relations 146, described herein.

The storage (e.g., hardware storage device(s) 140) also stores or includes computer-readable instructions 118 that are executable by the systems hardware processors for instantiating or implementing the disclosed models and/or engines shown in computing system 110 (e.g., the relation extraction model 147, the prediction module 148, and/or the supervision module 149).

The referenced models are configured as machine learning models or machine learned models, such as deep learning models and/or algorithms and/or neural networks. In some instances, the one or more models are configured as engines or processing systems (e.g., computing systems integrated within computing system 110), wherein each engine (i.e., model) comprises its own discrete set of one or more processors (e.g., hardware processor(s) 112) and computer-readable instructions 118.

Knowledge base data 141 is included in one or more knowledge bases (e.g., knowledge base(s) 126) that comprise known relation instances for a particular target relation. The knowledge bases are configured as a table comprising entity pairs and relation type between the different entity pairs. While the knowledge base is typically a human created database, these known relation instances included in the knowledge base are used to automatically annotate examples of the target relation (i.e., relation mentions) from unlabeled text. Co-occurring mention tuples of known relations are annotated as positive examples and those not known to have relations are sampled as negative examples. These examples of relation mentions are then used as training data (e.g., training data 142) to train a paragraph-level relation classifier included in the prediction module 148.

Thus, the knowledge base data 141 is used as training seed for teaching the relation extraction model, wherein the system is able to generate training data 142 based on the knowledge base data 141 being used to annotate a document. The knowledge base data 141 is used to create machine annotated text for training examples automatically. Thus, the training data 142 mostly comprises unlabeled text which is much more accessible than human or machine annotated text, wherein the unlabeled text is converted to annotated text using the knowledge base data 141. The system leverages the fact that paragraph-level distant supervision is much less noise prone (and requires no human annotation of input-output examples), but document-level relation mentions still observe similar textual patterns as paragraph-level ones, thus training remains effective for document-level relation extraction.

The knowledge bases are sparse databases that include a limited number of relation instances. The knowledge bases can also be robust databases that include many known relation instances. The knowledge bases do not include explicit input-output pairs, only the entity tuples that relate to the target relations corresponding to the knowledge bases. Inputs of the input-output pairs would be unlabeled (i.e., unannotated) text, while the corresponding output would be the annotated version of the text, including annotations for related entities. The knowledge base data 141 comprise the extracted related entities, without reference to the text from which they were extracted or learned.

The training data 142 is used for many training purposes, including training a relation extraction model 147 to perform document-level relation extraction through modular self-supervision. For example, the training data 142 is used to train the various modules included in the relation extraction model 147, such as the prediction module 148 and the supervision module 149. More specifically, the training data 142 comprise training data sets that are used to train a relation classifier that identifies a relation mention based on a target relation and extracts the relation mention as an initial relation that will be used as the basis for extracting a final relation from a target document. Such training datasets comprise input-output examples derived from annotations generated from using the knowledge base data 141.

The training data 142 also comprises training datasets for training a resolution classifier included in the prediction module 148 of the relation extraction model 147. The resolution classifier is trained to identify a set of entities (e.g., entities 143) within a document, at a whole document level, that are potentially related to each other and to the target relation (and/or initial relation). The resolution classifier is also trained on the training data 142 to identify related entities (e.g., related entities 144) within the set of entities and classify the related entities based on certain relation types (e.g., relation types 145).

The related entities 144 are typically binary pairs of related entities, wherein the entities included in the related pair of entities co-occur within the document. They can occur within a single sentence, a single paragraph, or within consecutive sentences, consecutive paragraphs. They can also occur as cross-paragraph relations. For example, a first entity is identified in a first paragraph, and a second entity related to the first entity is identified in a subsequent, non-consecutive paragraph (e.g., a third, fourth paragraph, etc.).

The entities are related based on the relation types 145. Different relation types include coreference relations, also ISA and PartOf relations. A coreference refers to an entity mention that is an alternate or substitute word for another entity mention, wherein both entity mentions correspond to the same entity. ISA relation types refer to entity mentions (e.g., words/phrases) that refer to the same entity. For example, the mutation "K57T" is a (ISA) MAP2K1 mutation or is a type of mutation occurring at the MAP2K1 gene. In another example, "Earth" ISA "planet". PartOf relation types refer to related entity pairs, wherein a first entity is related to a second entity because the first entity is a part of or a component of or a particular category of the second entity. For example, "Earth" is a part of (PartOf) the "Solar System". Other relation types include identical mentions and appositives, or entities that are related by applying the transitivity rule (e.g., if A relates to B, and B relates to C, then by the transitivity rule, A then relates to C). This is an example of joint inference.

The related entities 144 that are classified according to the relation types 145 are typically resolvable (e.g., the different entities can be resolved to generate a simplified map of related entities). One particular relation type, that is not resolved, but remains as a n-ary relation is a target relation (e.g., target relations 146). These target relations 146 are configured as entity tuples that have a specific relation desired to be extracted from a particular document. For example, a target relation for a drug response would include a drug, a gene, and a gene mutation, wherein the target relation describes whether the drug is effective for modifying the gene mutation occurring at the particular gene.

An additional storage unit for storing machine learning (ML) Engine(s) 150 is presently shown in FIG. 1 as storing a plurality of machine learning models and/or engines. For example, computing system 110 comprises one or more of the following: a data retrieval engine 151, a training engine 152, an evaluation engine 153, and an implementation engine 154, which are individually and/or collectively configured to implement the different functionality described herein.

For example, the data retrieval engine 151 is configured to locate and access data sources, databases, and/or storage devices comprising one or more data types from which the data retrieval engine 151 can extract sets or subsets of data to be used as training data or input audio data (e.g., new text data/document data). The data retrieval engine 151 receives data (e.g., knowledge base data 141 and/or unlabeled text) from the databases and/or hardware storage devices, wherein the data retrieval engine 151 is configured to reformat or otherwise augment the received data to be used as training data. Additionally, or alternatively, the data retrieval engine 151 is in communication with one or more remote systems (e.g., third-party system(s) 120) comprising third-party datasets and/or data sources (e.g., knowledge base(s) 126). In some instances, these data sources comprise audio-visual services that record or stream text, images, and/or video, wherein unlabeled text is extracted from the various media.

The data retrieval engine 151 accesses electronic content comprising unlabeled text data, labeled text data, ground truth transcription labels, ground truth relation mentions, and/or other types of audio-visual data including video data, image data, holographic data, 3-D image data, etc. The data retrieval engine 151 is configured to retrieve and generate training datasets comprising text data and corresponding annotations for a target relation. The data retrieval engine 151 is a smart engine that is able to learn optimal dataset extraction processes to provide a sufficient amount of data in a timely manner as well as retrieve data that is most applicable to the desired applications for which the machine learning models/engines will be trained. For example, the data retrieval engine 151 can learn which databases and/or datasets will generate training data that will train a model (e.g., for a specific query or specific task) to increase accuracy, efficiency, and efficacy of that model in the desired natural language processing techniques.

The data retrieval engine 151 locates, selects, and/or stores raw recorded source data such that the data retrieval engine 151 is in communication with one or more other ML engine(s) and/or models included in computing system 110. In such instances, the other engines in communication with the data retrieval engine 151 are able to receive data that has been retrieved (i.e., extracted, pulled, etc.) from one or more data sources such that the received data is further augmented and/or applied to downstream processes. For example, the data retrieval engine 151 is in communication with the training engine 152 and/or implementation engine 154.

The training engine 152 is in communication with one or more of the data retrieval engine 151, evaluation engine 153, and/or the implementation engine 154. In such embodiments, the training engine 152 is configured to receive one or more sets of training data 142 from the data retrieval engine 151. After receiving training data relevant to a particular application or task (e.g., a target relation), the training engine 152 trains one or more models on the training data. The training engine 152 is configured to train a model via unsupervised training, such as self-supervision, or distant supervision, and/or supervised training (i.e., direct supervision). The training engine 152 is figured to train the relation extraction model 147 on training data to modularly extract document-level relations.

To perform direction supervision, the training engine 152 utilizes training datasets that comprise explicit input-output pairs (e.g., unlabeled text and the corresponding annotations for related entities/a target relation). To perform semi-supervised training, the training engine 152 utilizes training datasets that comprise a limited number of input-output pairs and a large amount of unlabeled text. To perform distant supervision, which is a special case of self-supervision, the training engine 152 utilizes a complete and/or a sparsely populated knowledge base (also referred to as abstract knowledge) and a large amount of unlabeled text. The knowledge base data 141 is used to generate machine annotations for the unlabeled text, which are then used to train the relation extraction model 147, particularly the relation classifier of the relation extraction model 147.

The evaluation engine 153 is configured to evaluate the relation extraction model 147 during various relation extraction tasks. The evaluation engine 153 is used to optimize or further refine the model based on the evaluation results, and can be used as a test engine, wherein the relation extraction model 147 is first trained and then tested on separate test datasets. The evaluation engine 153 is configured to access one or more knowledge bases which contain high-quality document level annotations of drug-gene-mutations interactions, which have been manually curated from medical research articles. To avoid contamination between training datasets and evaluation datasets, the system removes entries whose documents from the evaluation datasets that also are used in the training and development stages.

The computing system 110 also includes an implementation engine 154 in communication with any one of the models and/or ML engine(s) 150 (or all of the models/engines) included in the computing system 110 such that the implementation engine 154 is configured to implement, initiate or run one or more functions of the plurality of ML engine(s) 150. In one example, the implementation engine 154 is configured to operate the data retrieval engines 151 so that the data retrieval engine 151 retrieves data at the appropriate time to be able to generate training data for the training engine 152. The implementation engine 154 facilitates the process communication and timing of communication between one or more of the ML engine(s) 150 and is configured to implement and operate a machine learning model (or one or more of the ML engine(s) 150).

The computing system is in communication with third-party system(s) 120 comprising one or more processor(s) 122, one or more of the computer-readable instructions 118, and one or more hardware storage device(s) 124. It is anticipated that, in some instances, the third-party system(s) 120 further comprise databases housing data that could be used as training data, for example, audio data not included in local storage. Additionally, or alternatively, the third-party system(s) 120 include machine learning systems external to the computing system 110. The third-party system(s) 120 are software programs or application.

Figure 2:
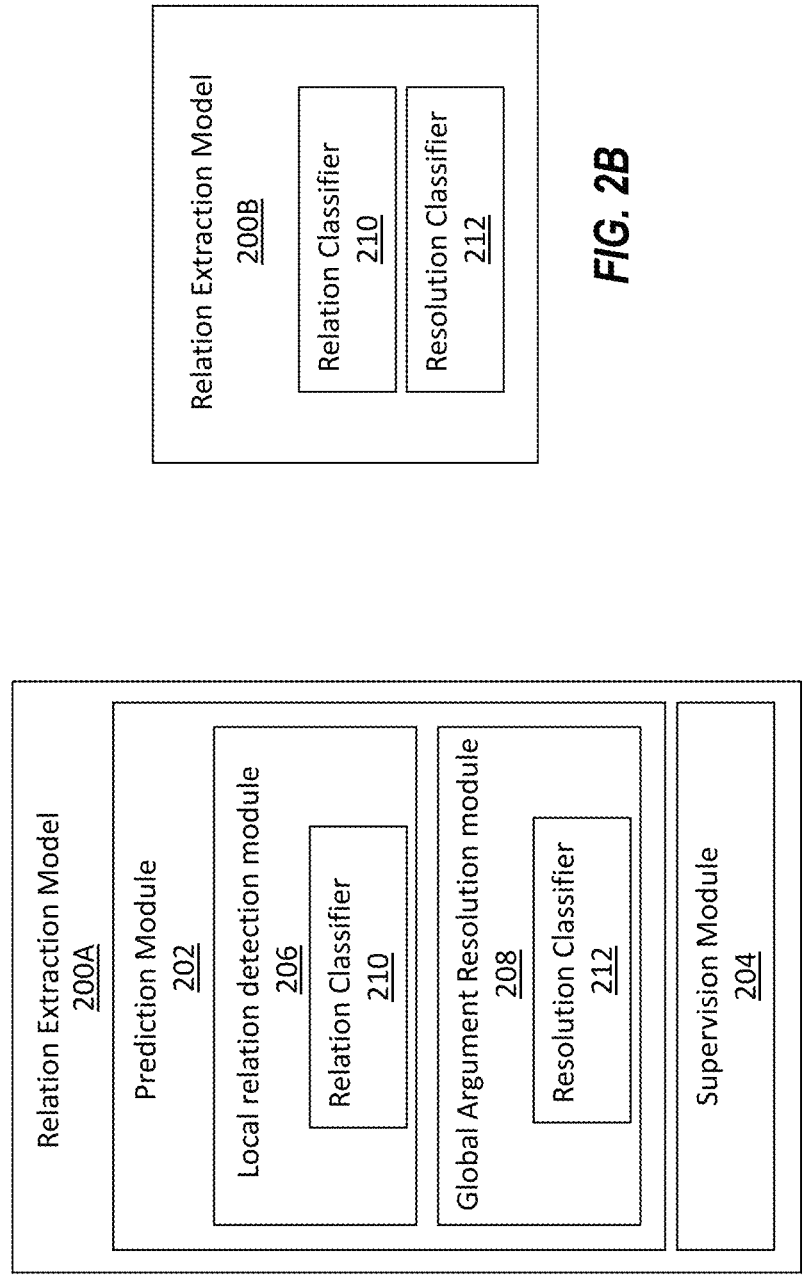
FIGS. 2A and 2B illustrate various example embodiments of the relation extraction model of FIG. 1.

Attention will now be directed to FIGS. 2A and 2B, which illustrate various example embodiments of a relation extraction model 200 (e.g., relation extraction model 147). For example, relation extraction model 200A is shown having a prediction module 202 (e.g., prediction module 148) and supervision module 204 (e.g., supervision module 149). The prediction module 202 is configured to predict a final relation associated with a document that corresponds to a target relation and includes a local relation detection module 206 and a global argument resolution module 208. The local relation detection module 206 is configured to identify an initial relation mention that corresponds to the target relation and includes a relation classifier 210 configured to identify the initial relation at a particular text-span level.

The global argument resolution module 208 is configured to identify entities that can be substituted in the initial relation to generate a final prediction for whether the target relation holds for the document and includes a resolution classifier 212 configured to identify related entities, classify the related entities based on the relation types, and resolve the various entities to generate a final relation. As shown in FIG. 2B, relation extraction model 200B is also shown as a simplified model comprising at least the relation classifier 210 and the resolution classifier 212.

Figure 3:
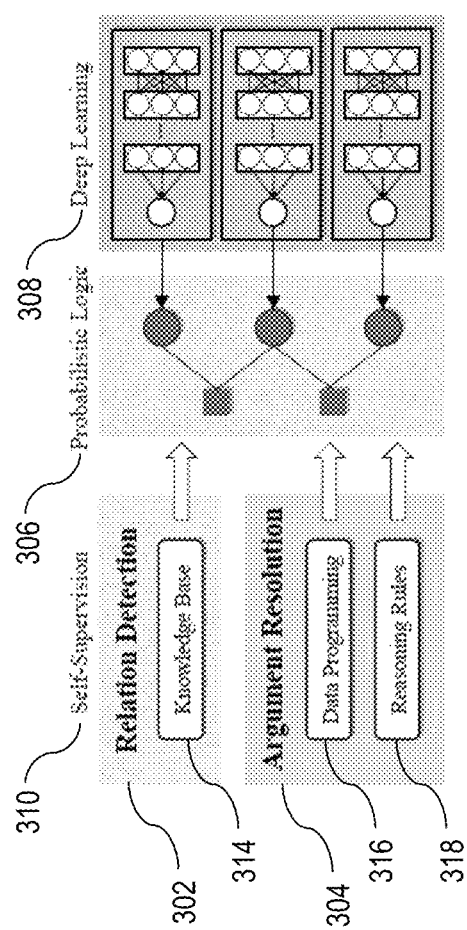
FIG. 3 illustrates an example embodiment for a process flow diagram for using probabilistic logic and deep learning to combine relation detection and argument resolution under self-supervision and with joint inference.

Attention will now be directed to FIG. 3, which illustrates an example embodiment of how the relation detection 302 and argument resolution 304 are implemented using probabilistic logic 306 and deep learning 308. To achieve document-level extraction, systems and methods are provided for modular self-supervision 310 for the different component problems (i.e., extracting the initial relation from a particular text span). Thus, the method includes applying probabilistic logic 306 to combine modular self-supervision 310 and joint inference which encompasses the argument resolution 304.

Probabilistic logic offers a principled way to soften self-supervision rules which are typically processed as hard constraints, and to model their noisiness. The relation detection 302 is self-supervised (e.g., distantly supervised) because it uses data retrieved from a knowledge base 314 to automatically generate machine annotated text that is used as training data for the relation classifier. The argument resolution 304 is achieved by using data programming 316 and reasoning rules 318 to resolve anaphoric occurrences of entities included in the initial relations detected by relation detection 302. Anaphora are instances of entity mentions that relate to the same entity.

The prediction module 202 and supervision module 204 define a joint probabilistic distribution. Learning is done via variational EM. In the E-step, the system computes a variational approximation using loopy propagation, based on the current state of the modules. In the M-step, the system treats the variational approximation as the probabilistic labels and refine parameters of the modules. The system treats the self-supervision in the supervision module 204 as hard constraints, so the M-step simplifies to fine-tuning the transformer-based models for relation detection and argument resolution, while still treating the variation approximation as probabilistic labels.

After training, given a test document and candidate entities and mentions, it is beneficial to run the neural modules for relation detection and argument resolution. Additionally, the system incorporates joint inference for argument resolution as in self-supervision using loopy propagation.

Figure 4:
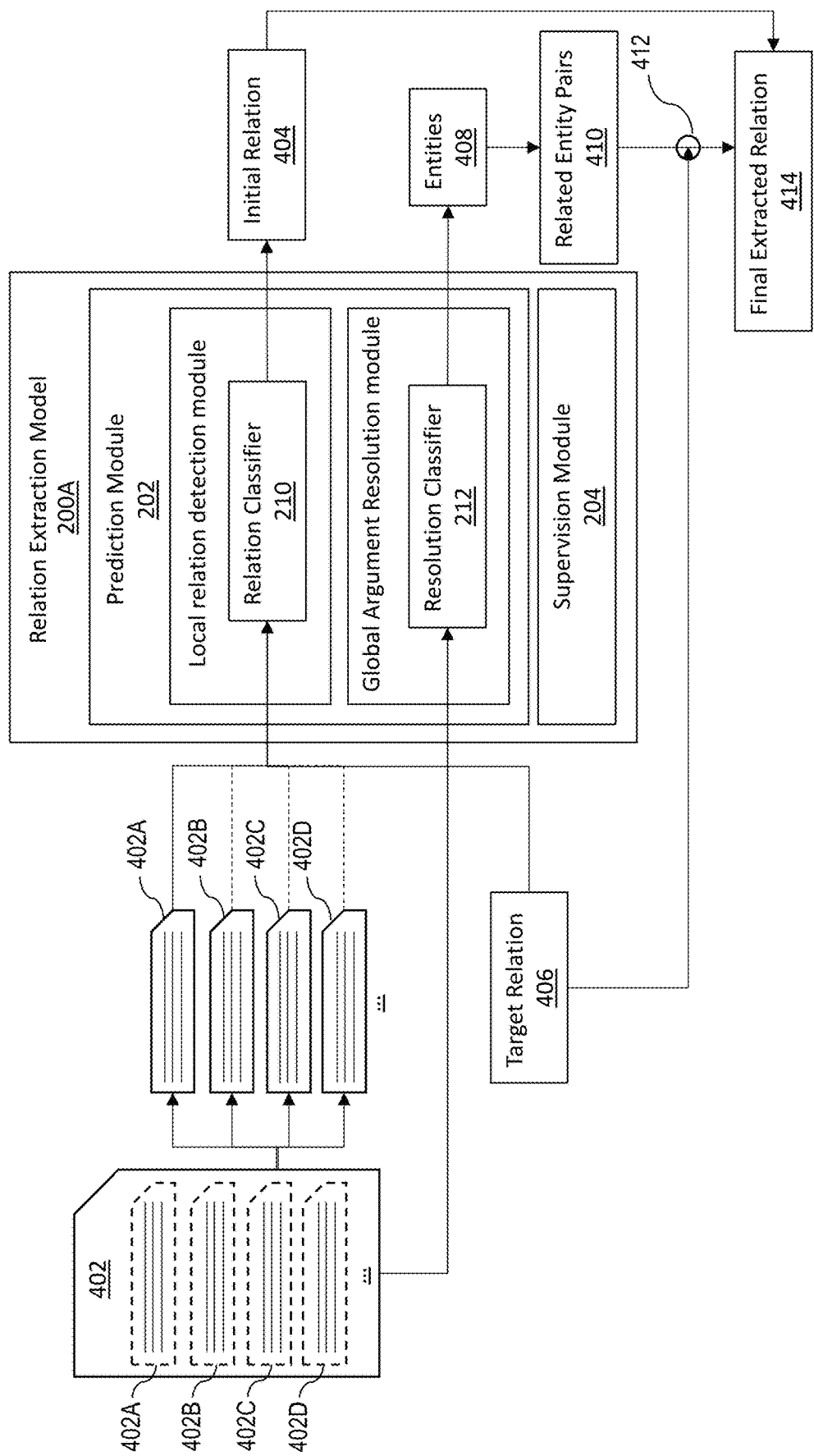
FIG. 4 illustrates an example embodiment for a process flow diagram for using a relation extraction model to extract document-level relations from a full-text article.

Attention will now be directed to FIG. 4, which illustrates an example embodiment for performing document-level relation extraction utilizing a relation extraction model as described herein. Like references to FIGS. 1, 2A-2B are used to show various related components in FIG. 4. The relation extraction model 200 is configured as a document-level relation extraction system that utilizes modular relation extraction. For example, the prediction module 202 comprises transformer based neural models for local relation detection and global argument resolution. The local relation detection module 206 is configured to detect relations within a local (i.e., limited) text span, which is a portion of the document that is less than the entire document. A document 402 is parsed into a plurality of text spans (e.g., text span 402A, text span 402B, text span 402C, and text span 402D). In some examples, each text span is a separate paragraph of the document. In other examples, each text span is a separate portion of a common paragraph within the document, such as multiple sentence of a paragraph. In other examples, each text span is a contiguous span of text of a predetermined length (e.g., n-characters). In other examples, each text span is a plurality of paragraphs from a document, or a plurality of sentences that span multiple paragraphs of the document. In some examples, each text span is a separate designated or classifiable portion of a document (e.g., summary, abstract, section, chapter, etc.)

Regardless of the type and size of text span that is used, each text span is applied to the relation classifier 210. The text spans are applicable to the relation classifier in any order, for example, consecutively, randomly, or based on detected relevancy.

The relation classifier 210 is a transformer-based classifier that is configured to receive a text span having a co-occurring mention tuple (i.e., an initial relation 404 comprising a set of co-occurring entities corresponding to a target relation 406) in that same text span. The mentions are typically masked before being applied to the relation classifier 210. Alternatively, the system adds entity markers for each mention included in the co-occurring mention tuple. Each text span is applied until the initial relation 404 is identified and extracted. In some examples, only an initial relation 404 is extracted from a particular text span. Alternatively, multiple initial relations are extracted from one or more text spans, wherein the system chooses the best initial relation to be used during argument resolution.

The global argument resolution module 208 is configured to resolve related entities that co-occur within the global environment of the document, wherein the resolution classifier 212 is configured to receive the document 402 in its entirety, identify related entities (e.g., related entity pairs 410) from a set of entities 408 co-occurring in the document, and classify the related entities based on various relation types. The related entities (i.e., related entity pairs) are then used to resolve one or more entities included in the initial relation (e.g., argument resolution 412) to generate a final extracted relation 414. For argument resolution, a candidate mention pair (e.g., a particular related entity pair) is selected. The system computes the contextual representation using a transformer model for both mentions and classifies the pair using a comparison network. The input concatenates contextual representations of the entities as well as their element-wise multiplication.

As shown, a text span is a reified event variable introduced to represent a relation, and the arguments are represented by binary relations with the event variable. The distributed nature of this representation makes it suitable for arbitrary n-ary relations and does not require drastic changes when arguments are missing or when new arguments are added. Given this representation, document-level relation extraction is naturally decomposed into local relation detection (e.g., classifying if a target relation holds for some text span) and global argument resolution (e.g., classifying various arguments).

Entry-level argument resolution can be reduced to mention-level argument resolution, where an entity mention signifies that a particular word is an entity mention of an entity. If two entities (or entity mentions) can be resolved, it means that the two words/phrases are interchangeable with one another with respect to the same entity. Entities can be resolved based on a relation type for coreferences, ISA, PartOf, as well as other semantically equivalent instances. Transitivity rules are also applied to resolve additional entities.

As described above, the supervision module 204 incorporates the relation knowledge bases and resolution data programming rules as seed self-supervision, as well as reasoning rules, such as resolution transitivity for joint inference. These self-supervision rules can be noisy, but are treatable as hard constraints, wherein applying deep probabilistic logic softens those constraints and mitigates the noise.

Attention will now be directed to FIG. 5, which illustrates an example of a relation comprising entities that co-occur at a document-level. Prior work on relation extraction tends to focus on binary relationships within sentences. However, practical applications often require extraction of complex relations across large text spans. This is especially important in high-value domains such as biomedicine, where obtaining high recall of the latest findings is crucial. For example, a ternary relation (drug, gene, mutation, represents that a tumor with MAP2K1 mutation K57T is sensitive to cobimetinib, yet the entities never co-occur in any single paragraph. For example, the final desired relation corresponding to a target relation (drug, gene, mutation) to be extracted from the example document 502 is (cobimetinib, MAP2K1, K57T). However, cobiminetib 506 occurs in a first text span 504, MAP2K1 510 occurs in a second text span 508, and MAP2K1 mutants 514 occurs in a third text span 512. The disclosed embodiments can be applied to such a document to extract the document-level relation from cross-paragraph entity mentions.

Figure 6A:
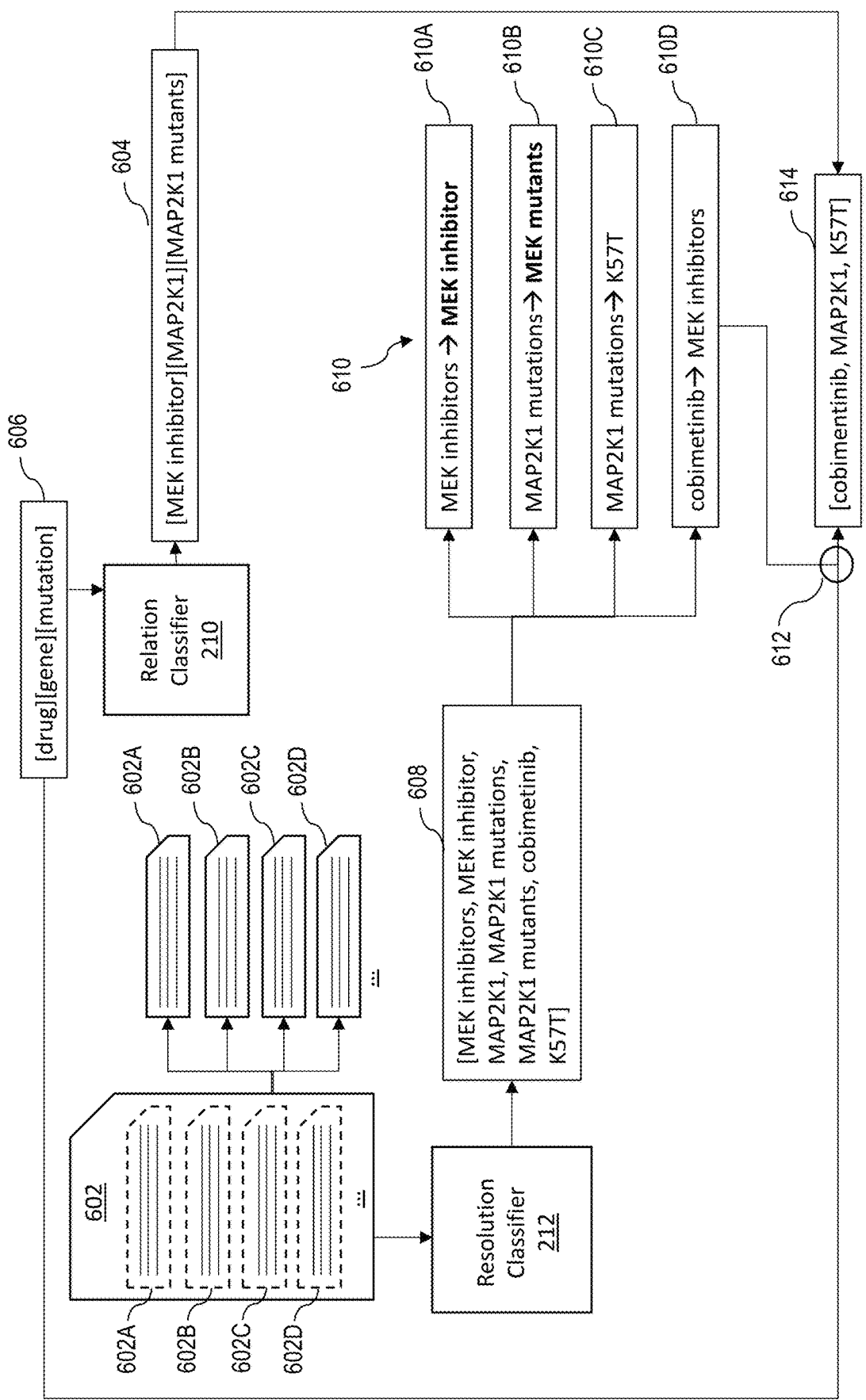
FIGS. 6A and 6B illustrate an example embodiment for a process flow diagram for using a relation extraction model to extract a document-level drug-gene-mutation relation from the document illustrated in FIG. 5.
Figure 6B:
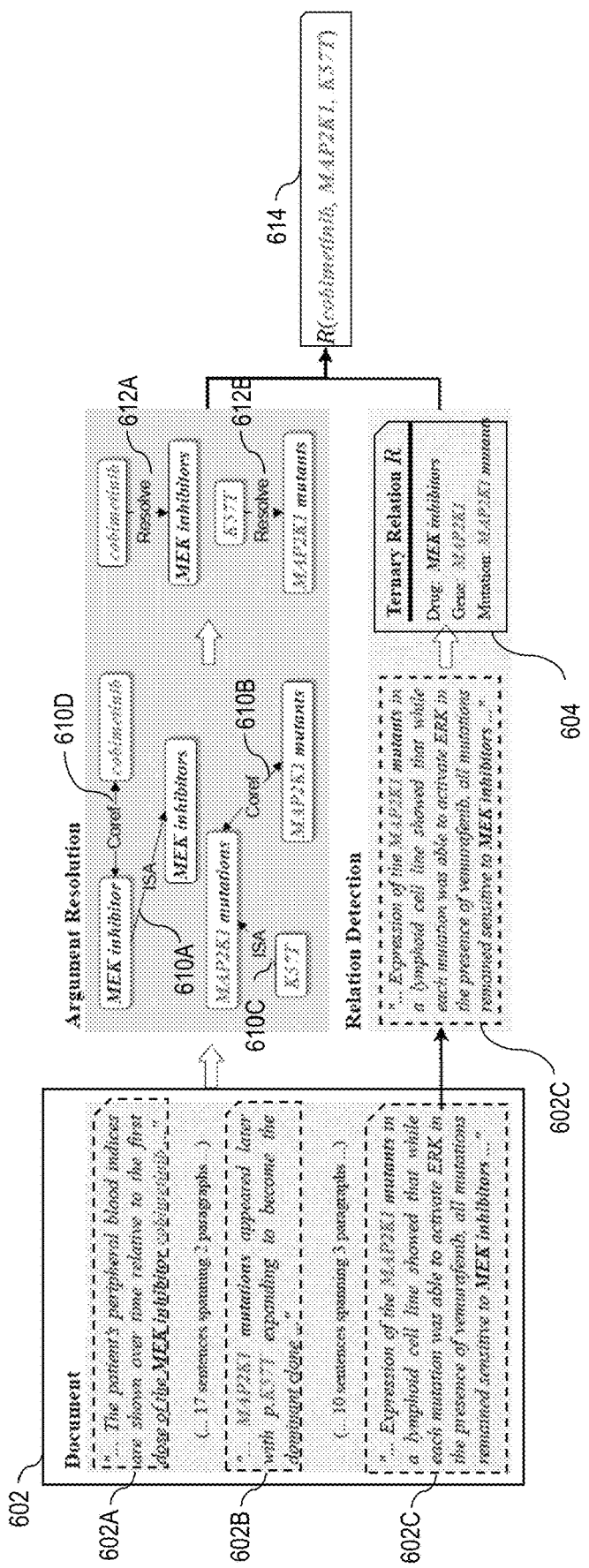

Attention will now be directed to FIGS. 6A and 6B, which illustrate example embodiments for using a relation extraction model as described herein to extract a document-level relation for a drug response relation 606, from a document like the one shown in FIG. 5. The drug response relation 606 is the target relation, which comprises a drug, a gene, and a gene mutation. The following example is focused on biomedical machine reading, where there is a pressing need for comprehensive extraction of the latest findings from full-text articles, and where cross-paragraph relation mentions are prevalent. Thus, FIGS. 6A and 6B show a solution to extraction precision oncology knowledge from a PubMed Central article, which is critical for molecular tumor boards and other precision health applications. Concretely, the goal is to extract drug-gene-mutation relations. Thus, given the target relation (drug, gene, mutation) and the document 602 in which they are mentioned, the system is able to determine whether the document 602 asserts that the mutation in the gene affects response to the drug.

The system comprising the relation classifier 210 and the resolution classifier 212 are previously trained on various datasets obtained from unlabeled documents from a medical research library database. For relation detection, the system derives distant supervision from a plurality of knowledge bases, with manually curated drug-gene-mutation relations. The system randomly splits the curated examples into training and development sets, ensuring no overlap of the documents within the separated training datasets. For argument resolution, the system uses global reasoning rules, such as transitivity, as well as data programming rules to capture anaphoric phenomena including identical mentions and appositions.

As shown in FIGS. 6A and 6B, document 602 (representative of document 502) is parsed into a plurality of text spans (e.g., text span 602A, text span 602B, text span 602C, and text span 602D). In this example, the selected/parsed text spans are separate paragraphs, or a certain number of consecutive sentences in the document 502. Each text span is applied to the relation classifier 210 until an initial relation is identified. As shown, when text span 602C is applied to the relation classifier 210, an initial relation 604 comprising MEK inhibitor (corresponding to the drug included in the target relation), MAP2K1 (corresponding to the gene included in the target relation, and MAP2K1 mutation (corresponding to the gene mutation included in the target relation). For self-supervised relation detection, the system decomposes the relation extraction into classifying drug-mutation relations and then augmenting them with high-precision gene mutation associations (to arrive at the initial relation 604).

However, a user may wish to further specify one or more entities included in the initial relation 604. In such instances, subsequently, or concurrently to applying the text spans to the relation classifier 210, the resolution classifier 212 receives the document 602 as whole to identify related entities (e.g., related entities 610) from a set of entities 608 co-occurring in the document 602 and classify the related entities based on various relation types. For example, the resolution classifier 212 identifies a set of entities 608, which are potentially related to one another and/or to one or more entities included in the target relation and/or initial relation. As shown in FIG. 6A, the set of entities 608 includes MEK inhibitors, MEK inhibitor, MAP2K1, MAP2K1 mutations, MAP2K1 mutants, cobimetinib, and K57T identified from the plurality of text spans, including text span 602A, 602B, and 602C.

The resolution classifier 212 then generates pairs of related entities 610. For example, related pair 610A comprises MEK inhibitor related to MEK inhibitors by the ISA relation type. Related pair 610B comprises MAP2K1 mutations related to MEK mutants by the ISA relation type. Related pair 610C comprises MAP2K1 mutations related to K57T by the coreference relation type. Related pair 610D comprises cobimetinib related to MEK inhibitors through the ISA relation type. As shown, each of these related pairs comprises entities co-occurring throughout the entire document.

The related entities (i.e., related entity pairs) are then used to resolve one or more entities included in the initial relation (e.g., argument resolution 612) to generate a final extracted relation 614. For example, MEK inhibitors included in the initial relation 604 is resolved (i.e., replaced) with cobimetinib (see argument resolution 612A) using the related pair 610D. Furthermore, MAP2K1 mutations is resolved with K57T (see argument resolution 612B) using the related pair 610C, related pair 6106, and a rule of transitivity (e.g., MEK mutants is resolved with MEK mutations, which is further resolved with K57T). One or more entities is resolved to a final state in order for the system to generate a final extracted relation 614 comprising cobimetinib, MAP2K1, and K57T.

In some instances, during training of the system, only named entities such as drug, gene, and mutation are considered; however, at inference time (e.g., run-time), in principle, any co-occurring noun phrases within a text span would be considered. This is computationally expensive in some tasks, so the system employs the following heuristics to leverage argument resolution results for filtering out candidates. In argument resolution, the system focuses on resolving candidate mentions with some named entities among drugs, genes, and mutations. The system constrains the candidate mention to having within it some relevant biomedical entity mentions (e.g., cell lines, genes etc. as in "MEK inhibitors" that contains gene reference MEK.) To save in computational strain, in relation detection, only candidate mentions that are classified as resolving with some named entities among drugs, genes, and mutations, based on the current prediction module.

Figure 7:
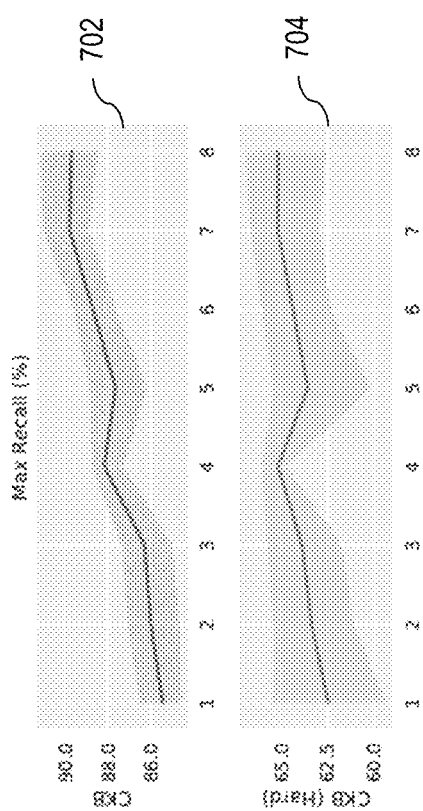
FIG. 7 illustrates various evaluation results of the disclosed embodiments for extracting document-level relations.

Attention will now be directed to FIG. 7, which illustrates how the disclosed argument resolution improves during learning as global reasoning rules augment seed self-supervision to raise maximum recall. From preliminary sample analysis, existing systems experience errors associated with relation extraction when some relation instances are hinted in figures, tables, or supplements. To address this problem/scenario, the disclosed systems are further trained on text extracted from figures, tables, and/or supplements, wherein the relation classifier is able to identify entities (and thus an initial relation) based on entity mentions occurring throughout the main text of the document, as well as any other audio-visual media included in the document. In other cases, the relation statement is vague and scattered, and relation detection required inference for piecing together multiple evidence sources.

Some conventional systems also experience errors that stem from argument resolution failures. For example, relation detection generally makes the right call, but argument resolution is mistaken. The disclosed systems overcome or address these errors by augmenting the self-supervision used in the resolution module (e.g., by applying the resolution classifier in the manner described herein). The beneficial effect of applying the disclosed techniques is quantifiable, as illustrated in FIG. 7. For example, in graph 702, the trend for max recall (%) (when implementing the disclosed embodiments) rises from 86.0 to almost 90.0. As shown in graph 704, the trend for max recall (%) (when implementing the disclosed embodiments and using hard constraints) rises from 62.5 to 65.0.

Figure 8:
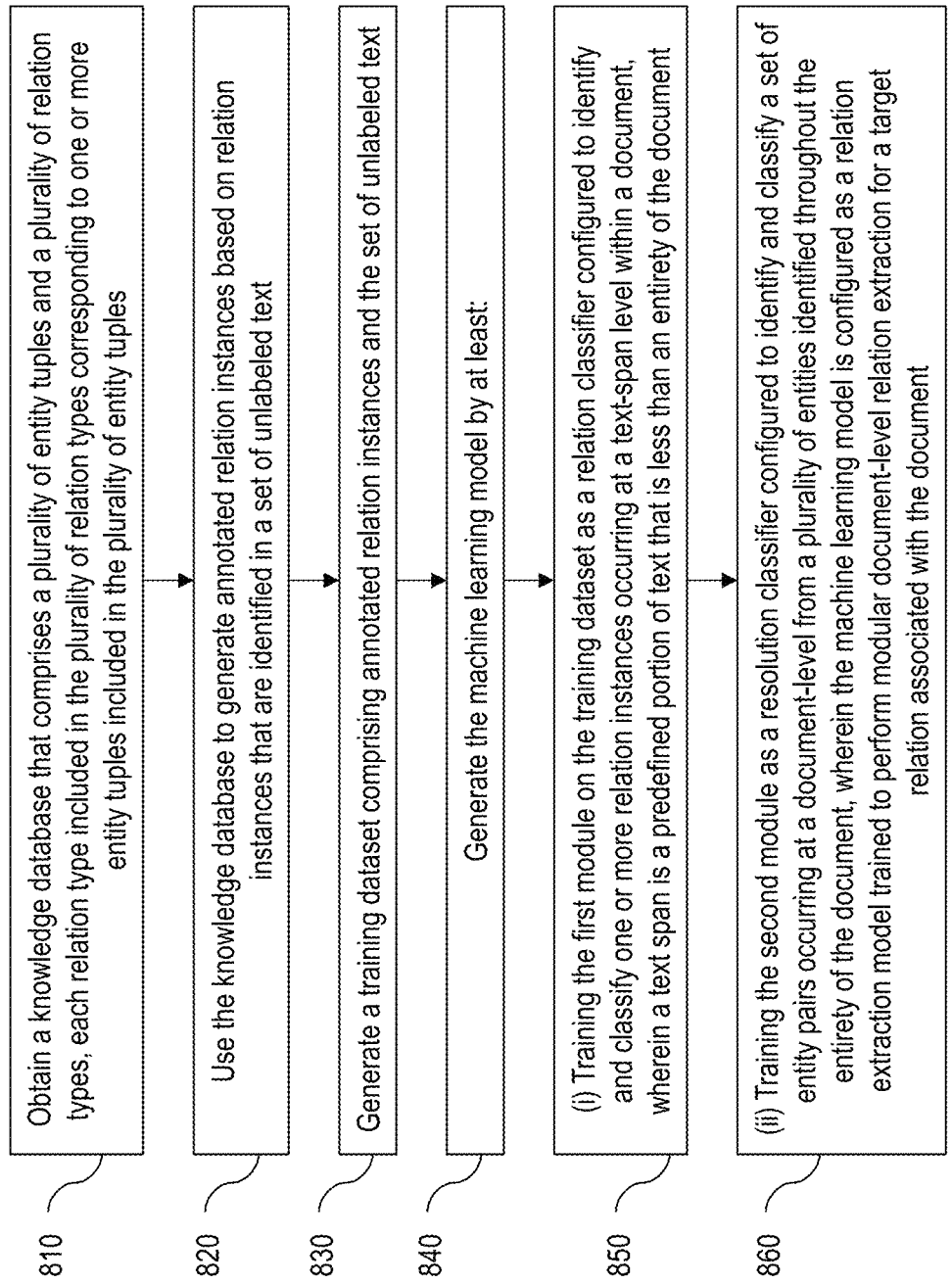
FIG. 8 illustrates an example embodiment of a flow diagram having a plurality of acts for generating training data and training a relation extraction model.
Figure 9:
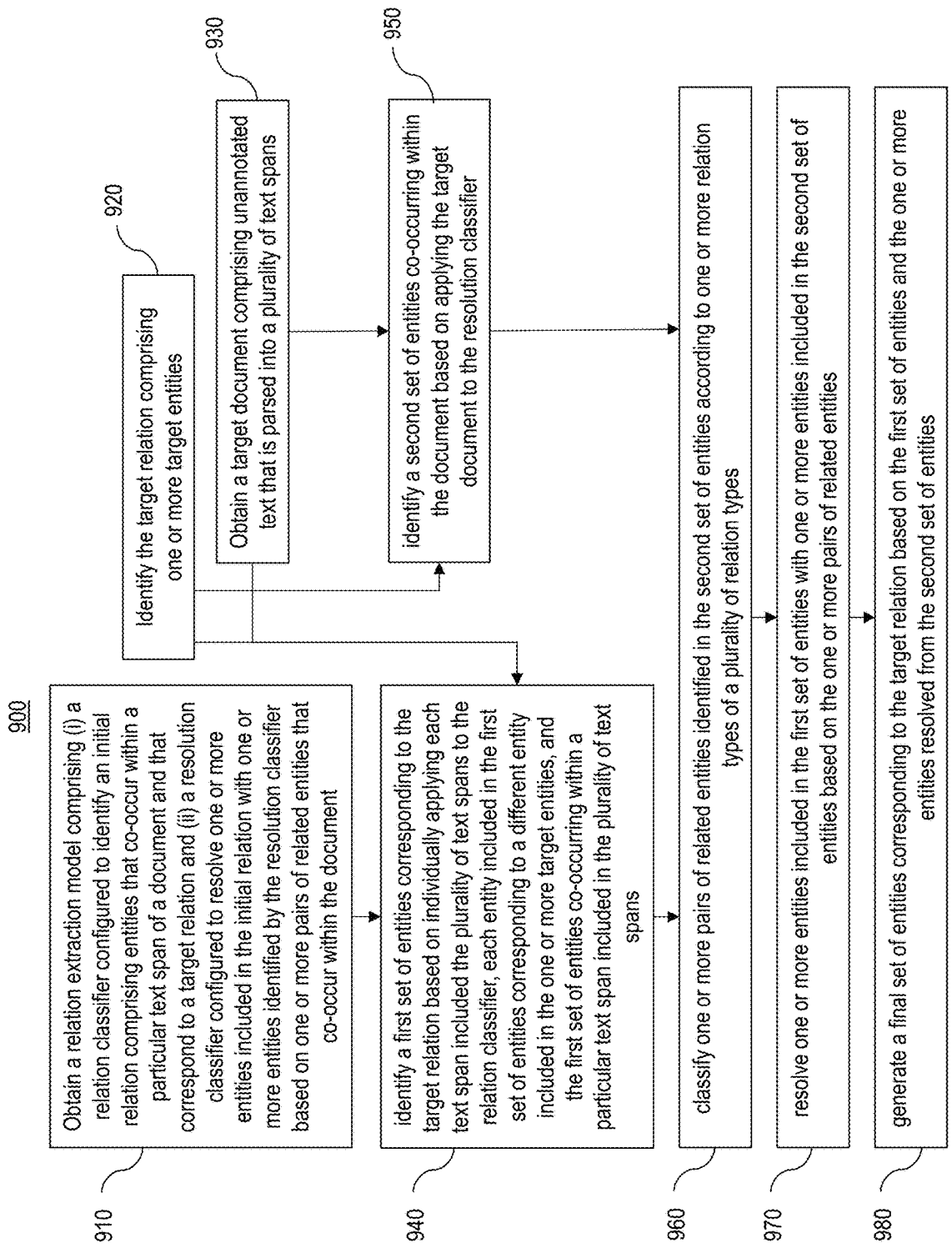
FIG. 9 illustrates an example embodiment of a flow diagram having a plurality of acts for using a trained relation extraction model at inference time.
Figure 10:
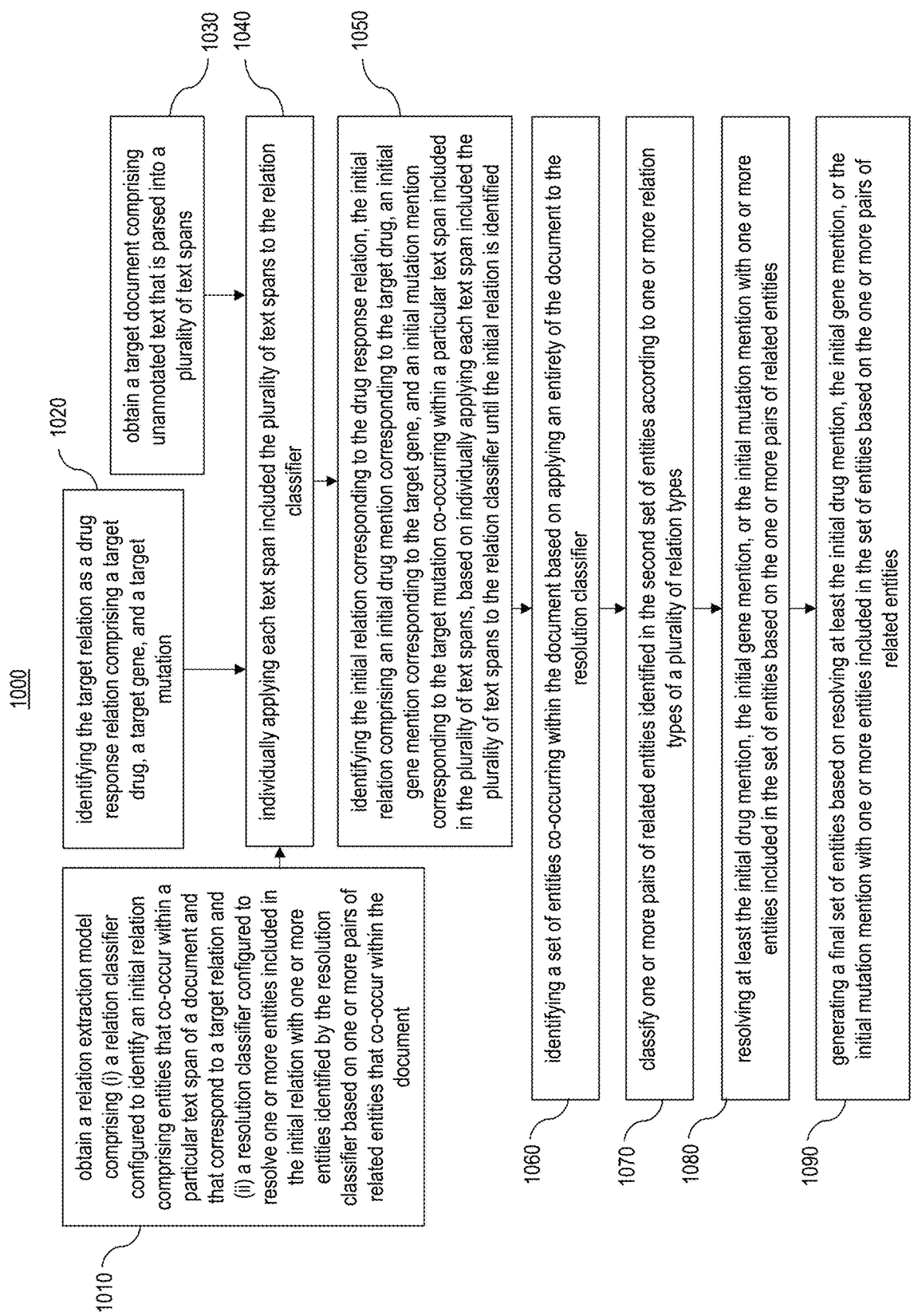
FIG. 10 illustrates an example embodiment of a flow diagram having a plurality of acts for using a relation extraction model to extract a document-level drug response relation.

Attention will now be directed to FIGS. 8-10, which illustrates various example embodiments of methods for performing the disclosed embodiments. Although the method acts may be discussed in a certain order or illustrated in a flow chart as occurring in a particular order, no ordering is required unless specifically stated, or required because an act is dependent on another act being completed prior to the act being performed.

Attention will now be directed to FIG. 8, in some reference to FIG. 1, which illustrates a flow diagram 800 that includes various acts (act 810, act 820, act 830, act 840, act 850, and act 860) associated with exemplary methods that can be implemented by computing system 110 for generating a machine learning model configured to extract document-level relations. As illustrated, the computing system first obtains a knowledge database that comprises a plurality of entity tuples and a plurality of relation types, each relation type included in the plurality of relation types corresponding to one or more entity tuples included in the plurality of entity tuples (act 810). The system then uses the knowledge database to generate annotated relation instances based on relation instances that are identified in a set of unlabeled text (act 820) and generates a training dataset comprising the annotated relation instances and the set of unlabeled text (act 830).

The computing system also generates the machine learning model (act 840) by at least: (i) training a first machine learning module on the training dataset as a relation classifier configured to identify and classify one or more relation instances occurring at a text-span level within a document, wherein a text span is a predefined portion of text that is less than an entirety of the document (act 850), and (ii) training the second module as a resolution classifier configured to identify and classify a set of entity pairs occurring at a document-level from a plurality of entities identified throughout the entirety of the document, wherein the machine learning model is configured as a relation extraction model trained to perform modular document-level relation extraction for a target relation associated with the document (act 860).

It will be appreciated that the relation extraction model is trainable under various supervision techniques. For example, the relation extraction model is trained using any combination of distant supervision, direct supervision, and/or semi-supervision.

To train the relation extraction model under direct supervision, the computing system obtains a direct supervision training dataset comprising a set of corresponding input/output pairs, wherein inputs of the set of corresponding input/output pairs comprise unlabeled text and outputs of the set of corresponding input/output pairs comprise annotated text with identified and classified relation instances and entity pairs and trains the relation extraction model with the direct supervision training dataset under direct supervision.

To train the relation extraction model under semi-supervision, the computing system obtains a semi-supervision training dataset comprising a limited set of corresponding input/output pairs and unannotated text, wherein inputs of the limited set of corresponding input/output pairs comprise unlabeled text and outputs of the limited set of corresponding input/output pairs comprise annotated text with identified and classified relation instances and entity pairs, and trains the relation extraction model with the semi-supervision training dataset under direct supervision.

Distant training includes the use of a knowledge database that is sparse and that does not include explicit input/output pairs of training data and/or that only includes weakly labeled training sets that are often labeled automatically based on heuristics/rules.

In a sparse knowledge base, the knowledge base includes less than approximately fifty pairs, or less than approximately ten pairs of related entities. The disclosed embodiments may use/apply knowledge bases that are sparse and knowledge bases that are robust (including hundreds or even thousands of relation examples).

In many instances, the knowledge database is a human generated table of entity pairs and relation types corresponding to the entity pairs or is a computer-generated table of entity pairs automatically extracted from a plurality of research articles and other sources. Additionally, or alternatively, at least some of the entity pairs and relation types in the knowledge database are generated automatically based on rules/heuristics.

Attention will now be directed to FIG. 9, which illustrates a flow diagram 900 that includes various acts (act 910, act 920, act 930, act 940, act 950, act 960, act 970 and act 980) associated with exemplary methods that can be implemented by computing system 110 for using a relation extraction model to extract document-level relations. The computing system obtains a relation extraction model comprising (i) a relation classifier configured to identify an initial relation comprising entities that co-occur within a particular text span of a document and that correspond to a target relation and (ii) a resolution classifier configured to resolve one or more entities included in the initial relation with one or more entities identified by the resolution classifier based on one or more pairs of related entities that co-occur within the document (act 910). The computing system also identifies the target relation comprising one or more target entities (act 920) and obtains a target document comprising unannotated text that is parsed into a plurality of text spans (act 930).

The computing system then identifies a first set of entities corresponding to the target relation based on individually applying each text span included the plurality of text spans to the relation classifier, each entity included in the first set of entities corresponding to a different entity included in the one or more target entities, and the first set of entities co-occurring within a particular text span included in the plurality of text spans (act 940).

The computing system identifies a second set of entities co-occurring within the document based on applying the target document to the resolution classifier (act 950) in order to classify one or more pairs of related entities identified in the second set of entities according to one or more relation types of a plurality of relation types (act 960). Finally, the computing system resolves one or more entities included in the first set of entities with one or more entities included in the second set of entities based on the one or more pairs of related entities (act 970) and generates a final set of entities corresponding to the target relation based on the first set of entities and the one or more entities resolved from the second set of entities (act 980).

The relation classifier of the relation extraction model is trained by: obtaining a knowledge database that comprises a plurality of entity tuples and a plurality of relation types, each relation type included in the plurality of relation types corresponding to one or more entity tuples included in the plurality of entity tuples, using the knowledge database to generate annotated relation instances based on relation instances that are identified in a set of unlabeled text, generating a training dataset comprising the annotated relation instances and the set of unlabeled text, and training the relation classifier on the training dataset such that the relation classifier is configured to identify and classify a set of relation instances at a text-span level.

It should also be appreciated that text spans are configurable according to customizable text span lengths. For example, each text span included in the plurality of text spans is a paragraph, or a pre-determined number of consecutive sentences.

Additionally, cross-paragraph relations occur when each entity included in a pair of the one or more pairs of related entities occurs in a different text span.

Regarding argument resolution, there are many different manners or relation types by which to resolve the different related entities. One or more entities included in the first set of entities are resolvable with one or more entities included in the second set of entities based on a pair of related entities that are identical mentions. One or more entities included in the first set of entities are resolvable with one or more entities included in the second set of entities based on a pair of related entities that are appositions. One or more entities included in the first set of entities with one or more entities included in the second set of entities based on a pair of related entities that are semantically equivalent co-references, and/or based on a pair of related entities that are alternate but equivalent terms corresponding to a "ISA" relationship type, and/or based on a pair of related entities that are alternate but equivalent terms corresponding to a "PartOf" relationship type. Additionally, or alternatively, one or more entities included in the first set of entities are resolvable with one or more entities included in the second set of entities based on a rule of transitivity being applied to two or more pairs of related entities.

Attention will now be directed to FIG. 10, which illustrates a flow diagram 1000 that includes various acts (act 1010, act 1020, act 1030, act 1040, act 1050, act 1060, act 1070, act 1080, and act 1090) associated with exemplary methods that can be implemented by computing system 110 for using a relation extraction model to extract document-level relations. The computing system first obtains a relation extraction model comprising (i) a relation classifier configured to identify an initial relation comprising entities that co-occur within a particular text span of a document and that correspond to a target relation and (ii) a resolution classifier configured to resolve one or more entities included in the initial relation with one or more entities identified by the resolution classifier based on one or more pairs of related entities that co-occur within the document (act 1010).

The computing system also identifies the target relation as a drug response relation comprising a target drug, a target gene, and a target mutation (act 1020) and obtains a document comprising unannotated text that is parsed into a plurality of text spans (act 1030). Subsequent to obtaining the document, the system individually applies each text span included the plurality of text spans to the relation classifier (act 1040) until it is able to identify the initial relation corresponding to the drug response relation, the initial relation comprising an initial drug mention corresponding to the target drug, an initial gene mention corresponding to the target gene, and an initial mutation mention corresponding to the target mutation co-occurring within a particular text span included in the plurality of text spans, based on individually applying each text span included the plurality of text spans to the relation classifier until the initial relation is identified (act 1050).

The computing system also identifies a set of entities co-occurring within the document based on applying an entirety of the document to the resolution classifier (act 1060) and classifies one or more pairs of related entities identified in the set of entities according to one or more relation types of a plurality of relation types (act 1070). Finally, the computing system resolves at least the initial drug mention, the initial gene mention, or the initial mutation mention with one or more entities included in the set of entities based on the one or more pairs of related entities (act 1080) and generates a final set of entities based on resolving at least the initial drug mention, the initial gene mention, or the initial mutation mention with one or more entities included in the set of entities based on the one or more pairs of related entities (act 1090). The computing system is also configured to determine whether the drug response relation holds for the final set of entities.

To further emphasize the technical benefits of the aforementioned systems and methods, in addition to the application for document-level extraction of n-ary relations, the disclosed embodiments facilitate improvements in discourse modeling. Given the focus of standard information extraction on short text spans, discourse modeling has not featured prominently in prior work. An exception is coreference resolution, though the focus tends to be improving sentence-level extraction. Disclosed embodiments provide systems and methods for document-level extraction using modeling the different anaphoric phenomena. Discourse modeling is further applied to the system in order to improve the argument resolution by reducing errors incurred during argument resolution (e.g., increased a maximum recall percentage).

Furthermore, task-specific self-supervision employed as part of the relation extraction disclosed herein alleviates the annotation bottleneck by leveraging freely available domain knowledge for use in creating training data for distant supervision training. To avoid the noise that arises from applying self-supervision to full-text articles, the disclosed embodiments are directed to a decomposed end-to-end document-level extraction, wherein the system leverages modular self-supervision that is much less error prone than conventional methods.

To improve inference and model learning, the system works to synergize the contrasting paradigms of logical approaches (rule-based or relational systems) to statistical and neural approaches. Such a system utilizes the linguistic structures and domain knowledge available. For example, neural logic programming replaces logical operators with neural representations to take advantage of domain-specific constraints with end-to-end differentiable learning.

Modular neural networks integrate component neural learning along a structured scaffold (e.g., syntactic parse of a sentence for visual question answering). Additionally, deep probabilistic logic combines probabilistic logic with neural networks to incorporate diverse self-supervision for deep learning. Overall, the system beneficially applies the modular neural networks and neural logic programming, in addition to deep probabilistic logic, to combine relation detection and argument resolution using global reasoning rules for document-level relation extraction.

In view of the foregoing, it will be appreciated that the disclosed embodiments provide many technical benefits over conventional systems and methods for building, training, and utilizing machine learning models for natural language processing including document-level relation extraction.

Embodiments of the present invention may comprise or utilize a special purpose or general-purpose computer (e.g., computing system 110) including computer hardware, as discussed in greater detail below. Embodiments within the scope of the present invention also include physical and other computer-readable media for carrying or storing computer-executable instructions and/or data structures. Such computer-readable media can be any available media that can be accessed by a general purpose or special purpose computer system. Computer-readable media (e.g., hardware storage device(s) 140 of FIG. 1) that store computer-executable instructions (e.g., computer-readable instructions 118 of FIG. 1) are physical hardware storage media/devices that exclude transmission media. Computer-readable media that carry computer-executable instructions or computer-readable instructions (e.g., computer-readable instructions 118) in one or more carrier waves or signals are transmission media. Thus, by way of example, and not limitation, embodiments of the invention can comprise at least two distinctly different kinds of computer-readable media: physical computer-readable storage media/devices and transmission computer-readable media.

Physical computer-readable storage media/devices are hardware and include RAM, ROM, EEPROM, CD-ROM or other optical disk storage (such as CDs, DVDs, etc.), magnetic disk storage or other magnetic storage devices, or any other hardware which can be used to store desired program code means in the form of computer-executable instructions or data structures and which can be accessed by a general purpose or special purpose computer.

A "network" (e.g., network 130 of FIG. 1) is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmission media can include a network and/or data links which can be used to carry, or desired program code means in the form of computer-executable instructions or data structures and which can be accessed by a general purpose or special purpose computer. Combinations of the above are also included within the scope of computer-readable media.

Further, upon reaching various computer system components, program code means in the form of computer-executable instructions or data structures can be transferred automatically from transmission computer-readable media to physical computer-readable storage media (or vice versa). For example, computer-executable instructions or data structures received over a network or data link can be buffered in RAM within a network interface module (e.g., a "NIC"), and then eventually transferred to computer system RAM and/or to less volatile computer-readable physical storage media at a computer system. Thus, computer-readable physical storage media can be included in computer system components that also (or even primarily) utilize transmission media.

Computer-executable instructions comprise, for example, instructions and data which cause a general-purpose computer, special purpose computer, or special purpose processing device to perform a certain function or group of functions. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, and the like. The invention may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Alternatively, or in addition, the functionality described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

The present invention may be embodied in other specific forms without departing from its essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A computing system comprising:
   one or more processors; and
   one or more hardware storage devices storing instructions that are executable by the one or more processors to cause the computing system to:
   obtain a relation extraction model comprising (i) a relation classifier configured to identify an initial relation comprising entities that co-occur within a particular text span of a document and that correspond to a target relation and (ii) a resolution classifier configured to resolve one or more entities included in the initial relation with one or more entities identified by the resolution classifier based on one or more pairs of related entities that co-occur within the document, wherein at least one text span includes a number of non-consecutive paragraphs distributed throughout text of the document, and wherein the relation extraction model, as a result of being trained, is configured to identify a relation instance that spans the non-consecutive paragraphs of the at least one text span such that the identified relation instance is identified by the relation extraction model as being a non-consecutive cross-paragraph relation instance;
   identify the target relation comprising one or more target entities;
   obtain a target document comprising unannotated text that is parsed into a plurality of text spans;
   identify a first set of entities corresponding to the target relation based on individually applying each text span included the plurality of text spans to the relation classifier, each entity included in the first set of entities corresponding to a different entity included in the one or more target entities, and the first set of entities co-occurring within a particular text span included in the plurality of text spans;
   identify a second set of entities co-occurring within the document based on applying the target document to the resolution classifier;
   classify one or more pairs of related entities identified in the second set of entities according to one or more relation types of a plurality of relation types;
   resolve one or more entities included in the first set of entities with one or more entities included in the second set of entities based on the one or more pairs of related entities, wherein said resolving is further performed using a resolution rule of transitivity for joint inference that is applied to two or more pairs of related entities, and wherein said resolution rule of transitivity for joint inference requires that when a first entity is related to a second entity and when the second entity is related to a third entity, then the first entity must also be related to the third entity; and
   generate a final set of entities corresponding to the target relation based on the first set of entities and the one or more entities resolved from the second set of entities.

2. The computing system of claim 1, wherein the relation classifier of the relation extraction model is trained by:
   obtaining a knowledge database that comprises a plurality of entity tuples and a plurality of relation types, each relation type included in the plurality of relation types corresponding to one or more entity tuples included in the plurality of entity tuples;
   using the knowledge database to generate annotated relation instances based on relation instances that are identified in a set of unlabeled text;
   generating a training dataset comprising the annotated relation instances and the set of unlabeled text; and
   training the relation classifier on the training dataset such that the relation classifier is configured to identify and classify a set of relation instances at a text-span level.

3. The computing system of claim 1, wherein each text span included in the plurality of text spans is a paragraph.

4. The computing system of claim 1, wherein each text span included in the plurality of text spans is a pre-determined number of consecutive sentences.

5. The computing system of claim 1, wherein each entity included in a pair of the one or more pairs of related entities occurs in a different text span.

6. The computing system of claim 1, wherein one or more entities included in the first set of entities are resolved with one or more entities included in the second set of entities based on a pair of related entities that are identical mentions.

7. The computing system of claim 1, wherein one or more entities included in the first set of entities are resolved with one or more entities included in the second set of entities based on a pair of related entities that are appositions.

8. The computing system of claim 1, wherein one or more entities included in the first set of entities are resolved with one or more entities included in the second set of entities based on a pair of related entities that are semantically equivalent co-references.

9. The computing system of claim 1, wherein one or more entities included in the first set of entities are resolved with one or more entities included in the second set of entities based on a pair of related entities that are alternate but equivalent terms corresponding to a "ISA" relationship type.

10. The computing system of claim 1, wherein one or more entities included in the first set of entities are resolved with one or more entities included in the second set of entities based on a pair of related entities that are alternate but equivalent terms corresponding to a "PartOf" relationship type.

11. A method implemented by a computing system for extracting a drug response relation from a document, the method comprising:
- obtaining a relation extraction model comprising (i) a relation classifier configured to identify an initial relation comprising entities that co-occur within a particular text span of a document and that correspond to a target relation and (ii) a resolution classifier configured to resolve one or more entities included in the initial relation with one or more entities identified by the resolution classifier based on one or more pairs of related entities that co-occur within the document, wherein at least one text span includes a number of non-consecutive paragraphs distributed throughout text of the document, and wherein the relation extraction model, as a result of being trained, is configured to identify a relation instance that spans the non-consecutive paragraphs of the at least one text span such that the identified relation instance is identified by the relation extraction model as being a non-consecutive cross-paragraph relation instance;
- identifying the target relation as a drug response relation comprising a target drug, a target gene, and a target mutation;
- obtaining a document comprising unannotated text that is parsed into a plurality of text spans;
- individually applying each text span included the plurality of text spans to the relation classifier;
- identifying the initial relation corresponding to the drug response relation, the initial relation comprising an initial drug mention corresponding to the target drug, an initial gene mention corresponding to the target gene, and an initial mutation mention corresponding to the target mutation co-occurring within a particular text span included in the plurality of text spans, based on individually applying each text span included the plurality of text spans to the relation classifier until the initial relation is identified;
- identifying a set of entities co-occurring within the document based on applying an entirety of the document to the resolution classifier;
- classifying one or more pairs of related entities identified in the set of entities according to one or more relation types of a plurality of relation types;
- resolving at least the initial drug mention, the initial gene mention, or the initial mutation mention with one or more entities included in the set of entities based on the one or more pairs of related entities, wherein said resolving is further performed using a resolution rule of transitivity for joint inference that is applied to two or more pairs of related entities, and wherein said resolution rule of transitivity for joint inference requires that when a first entity is related to a second entity and when the second entity is related to a third entity, then the first entity must also be related to the third entity; and
- generating a final set of entities based on resolving at least the initial drug mention, the initial gene mention, or the initial mutation mention with one or more entities included in the set of entities based on the one or more pairs of related entities.

12. The method of claim 11, further comprising:
determining whether the drug response relation holds for the final set of entities.

* * * * *